US010172572B2

(12) United States Patent
Jeong et al.

(10) Patent No.: US 10,172,572 B2
(45) Date of Patent: Jan. 8, 2019

(54) ASSIST DEVICE FOR ELASTOGRAPHY AND DIGITAL BREAST TOMOSYNTHESIS SYSTEM AND METHOD USING THE SAME FOR BREAST LESION DIAGNOSIS

(71) Applicant: Electronics and Telecommunications Research Institute, Daejeon (KR)

(72) Inventors: Ji Wook Jeong, Daejeon (KR); Seung-Hoon Chae, Daejeon (KR); Sooyeul Lee, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 212 days.

(21) Appl. No.: 15/408,271

(22) Filed: Jan. 17, 2017

(65) Prior Publication Data

US 2017/0238884 A1    Aug. 24, 2017

(30) Foreign Application Priority Data

Feb. 22, 2016    (KR) .................. 10-2016-0020739

(51) Int. Cl.
| | |
|---|---|
| *A61B 6/00* | (2006.01) |
| *A61B 6/04* | (2006.01) |
| *A61B 5/00* | (2006.01) |
| *A61B 6/02* | (2006.01) |

(52) U.S. Cl.
CPC .............. *A61B 6/04* (2013.01); *A61B 5/0051* (2013.01); *A61B 6/025* (2013.01); *A61B 6/502* (2013.01); *A61B 6/5235* (2013.01)

(58) Field of Classification Search
CPC combination set(s) only.
See application file for complete search history.

(56) References Cited

U.S. PATENT DOCUMENTS

| | | | |
|---|---|---|---|
| 7,940,889 B2* | 5/2011 | Hoheisel | A61B 6/0414 378/37 |
| 2007/0238966 A1 | 10/2007 | Sun et al. | |
| 2014/0012126 A1 | 1/2014 | Popescu | |
| 2015/0005631 A1 | 1/2015 | Jeong et al. | |
| 2015/0238113 A1 | 8/2015 | Son et al. | |

FOREIGN PATENT DOCUMENTS

KR    10-1067527 B1    9/2011

* cited by examiner

*Primary Examiner* — Dani Fox

(57) ABSTRACT

A digital breast tomosynthesis system includes an object fixing unit including first and second fixing plates, a first vibration plate moved in linkage with the first fixing plate and a second vibration plate moved in linkage with the second fixing plate, and configured to fix the object between the first and second vibration plates, an X-ray generator configured to project X-ray toward the object; an X-ray detector configured to detect the X-ray, a vibration generating device configured to vibrate the first and second vibration plates at a set frequency, and a vibration control device configured to control the vibration generating device by generating a vibration signal corresponding to the set frequency, wherein the X-ray generator projects the X-ray at specific time intervals on the basis of the set frequency.

18 Claims, 6 Drawing Sheets

ASSIST DEVICE FOR ELASTOGRAPHY AND DIGITAL BREAST TOMOSYNTHESIS SYSTEM AND METHOD USING THE SAME FOR BREAST LESION DIAGNOSIS

CROSS-REFERENCE TO RELATED APPLICATION

This U.S. non-provisional patent application claims priority under 35 U.S.C. § 119 to Korean Patent Application No. 10-2016-0020739, filed on Feb. 22, 2016, the entire contents of which are hereby incorporated by reference.

BACKGROUND

The present disclosure herein relates to a digital breast tomosynthesis (DBT), and more specifically, to an assist device for elastography and a digital breast tomosynthesis system and a method using the same for breast lesion diagnosis.

Recently, due to the advent of an aging era and improvement of people's living standard, early diagnosis and treatment of disease for healthy life has been gaining interest, and cancer among various diseases is the first major cause of death, and thereby has been the most important cause threatening national health. When classifying cancer incidence into categories, in case of men, stomach cancers, lung cancers, liver cancers, and colorectal cancers, which are the four major cancers and account for about 66% of the total male cancer incidence, have high occurrence ratios, in this order. On the contrary, in case of women, breast cancers, thyroid caners, stomach cancers, colorectal cancers, and lung cancers have high occurrence ratios in this order, and thus the breast cancers turn out to be occurring more frequently than the four major cancers. As such, in case of women, to diagnose in an early stage and treat the breast cancer having the highest occurrence ratio may be an important factor that should take precedence for a healthy life of a woman.

Among the diagnosis methods for breast cancers, mammography is a method mainly used for the breast cancer diagnosis for subclinical women. However, the mammography mainly used in typical cases is a technique using a two-dimensional image, and has many difficulties in detecting micro-calcification which is an important element for early diagnosis of breast cancer because a lesion of a target region is imaged to overlap normal tissues. Accordingly, the mammography has a low distinguishing capability and thereby has a high probability of generating a false positive or a false negative. Therefore, there are problems of accompanying additional inspection such as re-imaging or unnecessary biopsy to improve the accuracy of the diagnosis. To overcome these technical limitation in the breast cancer diagnosis technique using two-dimensional images, a digital breast tomosynthesis system (hereinafter, referred to as DBT) which is a breast cancer diagnosis technique using three-dimensional images is proposed.

Also, in elastography, which is recently developed and exhibits a preferential performance in the diagnosis of tumors, ultrasonic images are captured while a specific surface of a human body is vibrated at several ten Hz from the outside. The elastography reconstructs an elastic feature image from the difference between the ultrasonic images captured at this time to thereby visualize an elastic feature image of a human body, and thus has received attention as a functional ultrasonic image.

SUMMARY

The present disclosure provides an assist device for elastography used for a digital breast tomosynthesis system. The present disclosure also provides a system and a method for digital breast tomosynthesis using the assist device for elastography in order to obtain an ordinary DBT image and an elastic image.

An embodiment of the inventive concept provides a digital breast tomosynthesis system includes: an object fixing unit including first and second fixing plates, a first vibration plate moved in linkage with the first fixing plate and a second vibration plate moved in linkage with the second fixing plate, and configured to fix the object between the first and second vibration plates; an X-ray generator configured to project X-ray toward the object; an X-ray detector configured to detect the X-ray; a vibration generating device configured to vibrate the first and second vibration plates at a set frequency; and a vibration control device configured to control the vibration generating device by generating a vibration signal corresponding to the set frequency, wherein the X-ray generator projects the X-ray at specific time intervals on the basis of the set frequency.

In an embodiment, the vibration control device may provide vibration displacement information about the first and second vibration plates to determine the specific time intervals.

In an embodiment, digital breast tomosynthesis system may further include a displacement measuring device configured to generate the vibration displacement information for measuring displacements of the first and second vibration plates.

In an embodiment, the X-ray generator may determine the specific time intervals on the basis of the vibration displacement information received from the displacement measuring device.

In an embodiment, the specific time intervals may be set to equal intervals for one period of a vibration displacement of the object.

In an embodiment, the specific time intervals may include a plurality of time intervals changing according to a setting for the one period of a vibration displacement of the object.

In an embodiment, the greater a width of the vibration displacement of the object, the greater the time intervals, the specific time intervals may have.

In an embodiment, the X-ray detector may be positioned on the reverse side of the X-ray generator with respect the object, and the X-ray generator and the X-ray detector may be rotated around the object according to a set angle.

In an embodiment, the vibration generating device may include: a first fluid container positioned between the first fixing plate and the first vibration plate; a second fluid container positioned between the second fixing plate and the second vibration plate; and a fluid control device configured to adjusting a fluid pressure of a buffer fluid filled into the first and second containers, wherein the fluid control device may control the fluid pressure of the buffer fluid such that the first and second vibration plates vibrate at the set frequency according to the vibration control signal.

In an embodiment, the vibration generating device may include a vibrator for vibrating the first and second vibration plates at the set frequency according to the vibration control signal.

In an embodiment of the inventive concept, a vibration generation assist device used for a digital breast tomosynthesis system for capturing an X-ray image of an object, includes: an object fixing unit including first and second fixing plates, a first vibration plate moved in linkage with the first fixing plate and a second vibration plate moved in linkage with the second fixing plate, and configured to fix the object between the first and second vibration plates; a first fluid container positioned between the first fixing plate and the first vibration plate; a second fluid container positioned between the second fixing plate and the second vibration plate; and a fluid control device configured to adjusting a fluid pressure of a buffer fluid filled into the first and second containers, wherein the fluid control device controls the fluid pressure of the buffer fluid such that the first and second vibration plates vibrate at the set frequency according to the vibration control signal.

In an embodiment, the first and second fluid containers may be formed of a soft film and thereby have sizes varying with the fluid pressure of the buffer fluid corresponding to the set frequency.

In an embodiment, the vibration generation assist device may further include a vibration guide connected to the first and second vibrating plates to control the first and second plates so as to vibrate in a specific direction.

In an embodiment, the first and second vibration plates may vibrate synchronously with each other according to the set frequency.

In an embodiment of the inventive concept, a digital breast tomosynthesis method for a digital breast tomosynthesis system which comprises first and second fixing plates, a first vibration plate moved in linkage with the first fixing plate and a second vibration plate moved in linkage with the second fixing plate, and configured to fix an object between the first and second vibration plates, includes: setting positions of the first and second fixing plates and the first and second vibration plates; setting a measuring angle for irradiating the object with X-ray; determining whether to measure an elastic image; vibrating the first and second vibration plates according to a set vibration frequency when the elastic image is measured; measuring vibration displacements of the first and second vibration plates; obtaining a plurality of X-ray images by irradiating the object with the X-ray according to the vibration displacements; and generating the elastic image on the basis of the X-ray images.

In an embodiment, in determining whether to measure the elastic image, when the elastic image is not measured, the object may be irradiated with the X-ray without vibrating the first and second vibration plates.

In an embodiment, the digital breast tomosynthesis method may further include ensuring whether measuring is completed for all the set measuring angles, wherein when the measuring is not completed for all the set measuring angles, the measuring angle may be changed, and the determining whether to measure the elastic image to the generating the elastic image may be repeated.

In an embodiment, when the measuring is completed for all the set measuring angles, an elastic digital breast tomosynthesis (DBT) image may be generated on the basis of the plurality of X-ray images.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
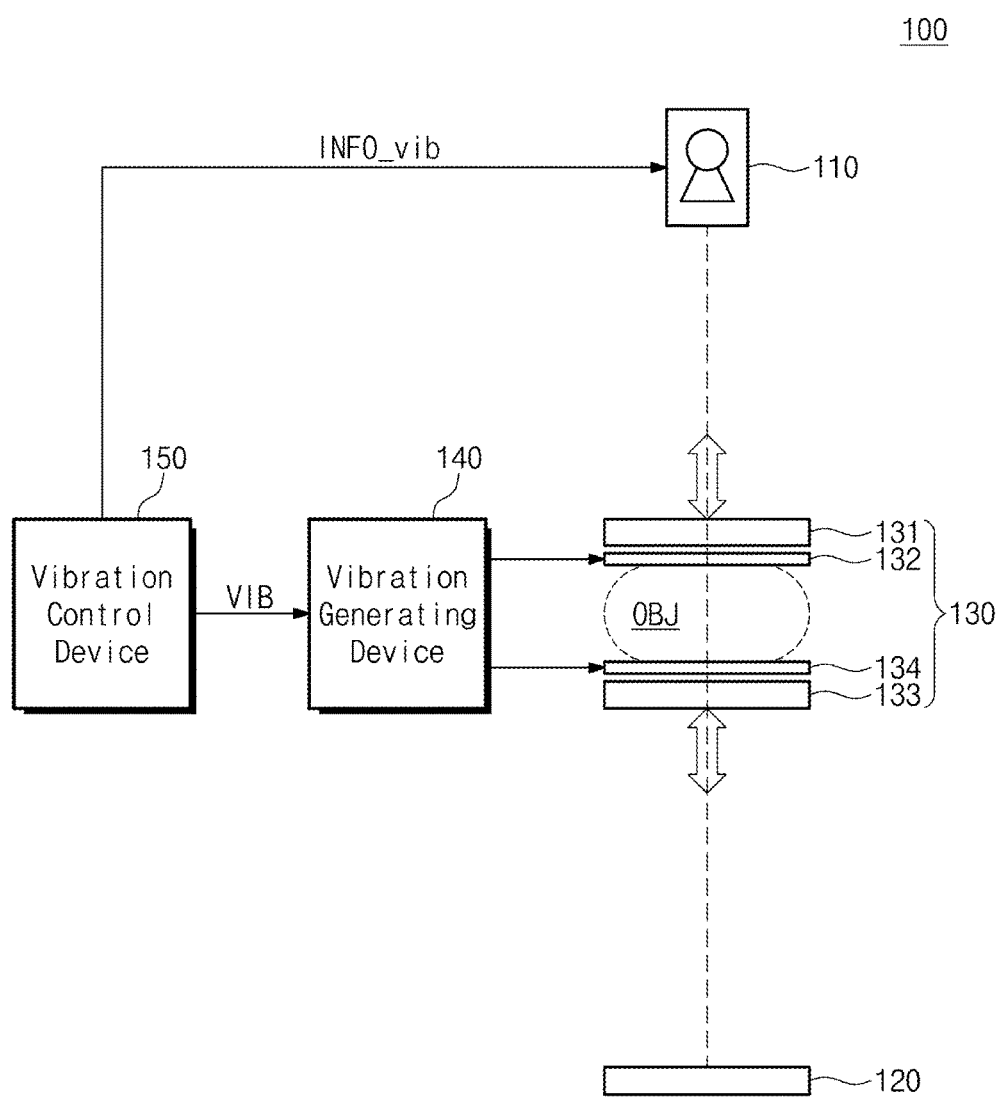
FIG. 1 is a view illustrating a digital breast tomosynthesis system according to an embodiment of the inventive concept.

It should be construed that foregoing general illustrations and following detailed descriptions are exemplified and an additional explanation of claimed inventive concept is provided. Reference numerals are indicated in detail in preferred embodiments of the inventive concept, and their examples are represented in reference drawings. In every possible case, like reference numerals are used for referring to the same or similar elements in the description and drawings.

Hereinafter, a digital breast tomosynthesis system is used as an example for describing characteristics and functions of the inventive concept. However, those skilled in the art can easily understand other advantages and performances of the inventive concept according to the descriptions. The inventive concept may be embodied or applied through other embodiments. Besides, the detailed description may be amended or modified according to viewpoints and applications, not being out of the scope, technical idea and other objects of the present invention.

FIG. 1 is a view illustrating a digital breast tomosynthesis system according to an embodiment of the inventive concept. Referring to FIG. 1, a digital breast tomosynthesis system 100 may include an X-ray generator 110, an X-ray detector 120, an object fixing unit 130, a vibration generating device 140, and a vibration control device 150. Hereinafter, the object OBJ is assumed as a breast. However, the object OBJ is not limited thereto. Any portion of a human body may be the object. The X-ray generator 110 generates X-ray to irradiate the object OBJ. For example, the X-ray generator 110 may include an X-ray tube. X-ray projected from the X-ray generator 110 may include photons having a plurality of energy levels.

X-ray may be projected from the X-ray generator 110 over a plurality of times for a specific time period. For example, X-ray may be projected from the X-ray generator 110 about 20 times to about 30 times for one second. X-ray may be projected from the X-ray generator 110 at regular intervals for a specific time period. X-ray may be projected from the X-ray generator 110 at intervals different from each other for a specific time period.

The X-ray generator 110 may receive vibration displacement information INFO_vib from the vibration control device 150. For example, the X-ray generator 110 may adjust the number and intervals of X-ray projection on the basis of the vibration displacement information INFO_vib. The X-ray may be projected from the X-ray generator 110 synchronously with the vibration of a first vibration plate 132 and the second vibration plate 134 on the basis of the vibration displacement information INFO_vib.

The X-ray detector 120 may detect X-ray image passing through the object OBJ. For example, the X-ray detector 120 may detect photons projected from the X-ray generator 110 and may thereby obtain X-ray image passing through the object OBJ. The X-ray detector 120 may include an X-ray detecting element. As the X-ray detecting element, an amorphous silicon (a-Si) type, a complementary metal oxide silicon (CMOS) type, an amorphous selenium (a-Se) type, or the like may be used. For the amorphous silicon type and the CMOS type, a method of firstly converting X-ray into visible light by using a planar scintillator and then converting the visible light again into an electrical signal. On the contrary, for the amorphous selenium type, a method of directly converting X-ray into an electrical signal by using a photoelectric phenomenon is used. For example, the X-ray detector 120 has a plurality of detecting elements arrayed in a two-dimensional shape. The X-ray detector 120 may be located at the reverse side to the X-ray generator 110 with respect to the object OBJ.

The object fixing unit 130 may fix the object OBJ. Also, the object fixing unit 130 may compress the object OBJ. For example, the fixing part 130 may include a first fixing plate 131, a first vibrating plate 132, a second fixing plate 133, and a second vibrating plate 134. The first and second fixing plates 131 and 133 may be moved in the vertical direction. The object OBJ may be fixedly positioned or compressed through the movements of the first and second fixing plates 131 and 133. The first and second fixing plates 131 and 133 may be rotated around the object OBJ.

The first vibration plate 132 may be vertically moved in linkage with the first fixing plate 131. The second vibration plate 134 may be vertically moved in linkage with the second fixing plate 133. The object OBJ may be fixedly positioned or compressed between the first and second vibration plates 132 and 134. The first and second vibrating plates 132 and 134 may be vibrated according to the control of the vibration generating device 140.

The vibration generating device 140 may vibrate the first and second vibrating plates 132 and 134 in response to a vibration control signal VIB. For example, the vibration control signal VIB may be a voltage signal. The vibration generating device 140 may adjust the vibration frequency of the first and second vibrating plates 132 and 134 according to the voltage level of the vibration control signal VIB.

The vibration control device 150 may control the overall operation of the vibration generating device 140. For example, the vibration control device 150 may generate the vibration control signal VIB according to a target frequency. The vibration control device 150 may store the value of the vibration control signal VIB corresponding to a vibration frequency in a look-up table form. Also, the vibration control device 150 may provide the X-ray generator 110 with the vibration displacement information INFO_vib. The vibration displacement information INFO_vib may include the vibration frequency information of the first and second vibrating plates 132 and 134.

The digital breast tomosynthesis system 100 according to an embodiment of the inventive concept may provide an X-ray image by irradiating the object OBJ with X-ray. Also, X-ray may be projected from the digital breast tomosynthesis system 100 synchronously with the vibration of the first and second vibrating plates 132 and 134. In the digital breast tomosynthesis system 100, a plurality of X-ray images synchronized with the vibration of the first and second vibrating plates 132 and 134 may be obtained. Accordingly, in the digital breast tomosynthesis system 100, an X-ray elastic image may be obtained by reconstructing the obtained X-ray images.

Figure 2:
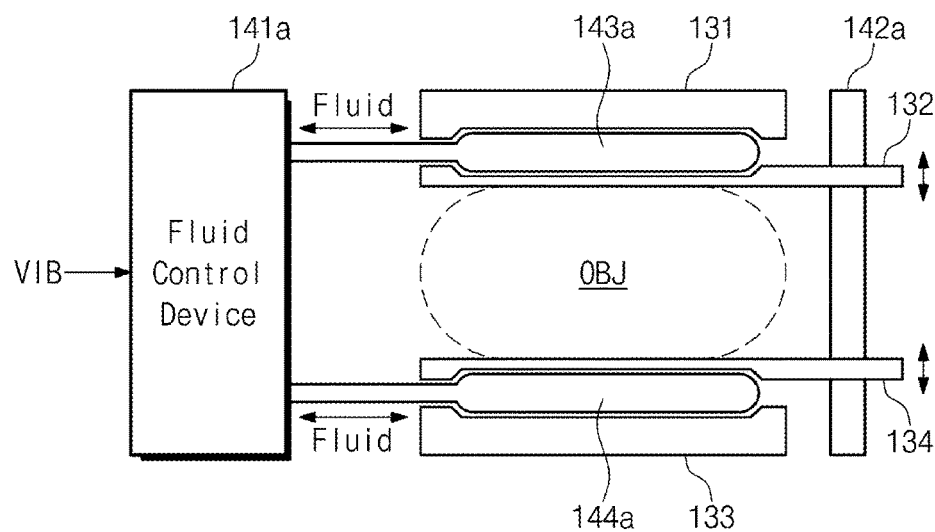
FIG. 2 is a view illustrating an embodiment of a vibration generating device of FIG. 1.

FIG. 2 is a view illustrating an embodiment of a vibration generating device of FIG. 1. Referring to FIG. 2, the vibration generating device 140 of FIG. 1 may include a fluid control device 141a, a vibration guide 142a, a first fluid container 143a, and a second fluid container 144a. The vibration generating device 140 may vibrate the first and second vibrating plates 132 and 134 in response to a vibration control signal VIB.

The fluid control device 141a may inject/extract a buffer fluid into/from the first and second fluid containers 143a and 144a. The fluid control device 141a may receive a vibration control signal VIB. For example, the fluid control device 141a may control the pressure of the buffer fluid in the first and second fluid containers 143a and 144a on the basis of the vibration control signal VIB. The fluid control device 141a may adjust the change in the pressure of the buffer fluid to thereby vibrate the first and second vibrating plates 132 and 134. When the vibration frequency is increased, the fluid control device 141a may quickly change the pressure of the buffer fluid. When the vibration frequency is decreased, the fluid control device 141a may slowly change the pressure of the buffer fluid.

The first and second vibrating plates 132 and 134 may vertically vibrate along the vibration guide 142a. Due to the vibration guide 142a, the first and second vibrating plates 132 and 134 may transmit vibration to an object OBJ in a constant direction.

The first fluid container 143a may be formed as a soft film. For example, the first fluid container 143a may be formed of a material capable of constantly transmitting the pressure of the buffer fluid to the first vibrating plate 132, such as rubber or silicone. Also, the first fluid container 143a may be connected to the fluid control device 141a through a connecting tube which is a moving passage of the buffer fluid. Also, the second fluid container 144a may be formed in the same manner as the first fluid container 143a.

Figure 3:
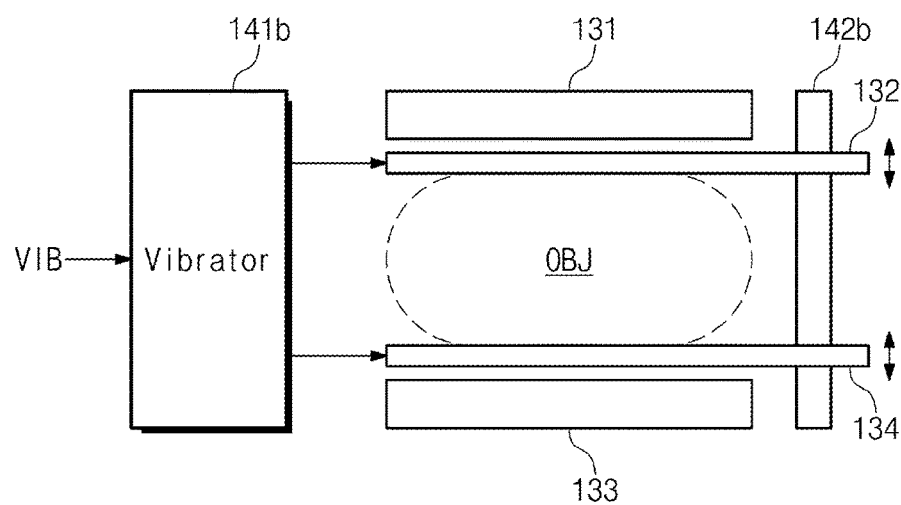
FIG. 3 is a view illustrating another embodiment of a vibration generating device of FIG. 1.

FIG. 3 is a view illustrating another embodiment of the vibration generating device of FIG. 1. Referring to FIG. 3, the vibration generating device 140 of FIG. 1 may include a vibrator 141b and a vibration guide 142b. The vibration generating device 140 may vibrate the first and second vibrating plates 132 and 134 in response to a vibration control signal VIB.

The vibrator 141b may receive the vibration control signal VIB. For example, the vibrator 141b may vibrate the first and second vibrating plates 132 and 134 in response to the vibration control signal VIB. When the vibration frequency is increased, the vibrator 141b may quickly vibrate the first and second vibrating plates 132 and 134. When the vibration frequency is decreased, the vibrator 141b may slowly vibrate the first and second vibrating plates 132 and 134.

The first and second vibrating plates 132 and 134 may vertically vibrate along the vibration guide 142b. Due to the vibration guide 142b, the first and second vibrating plates 132 and 134 may transmit vibration to an object OBJ in a constant direction.

Figure 4:
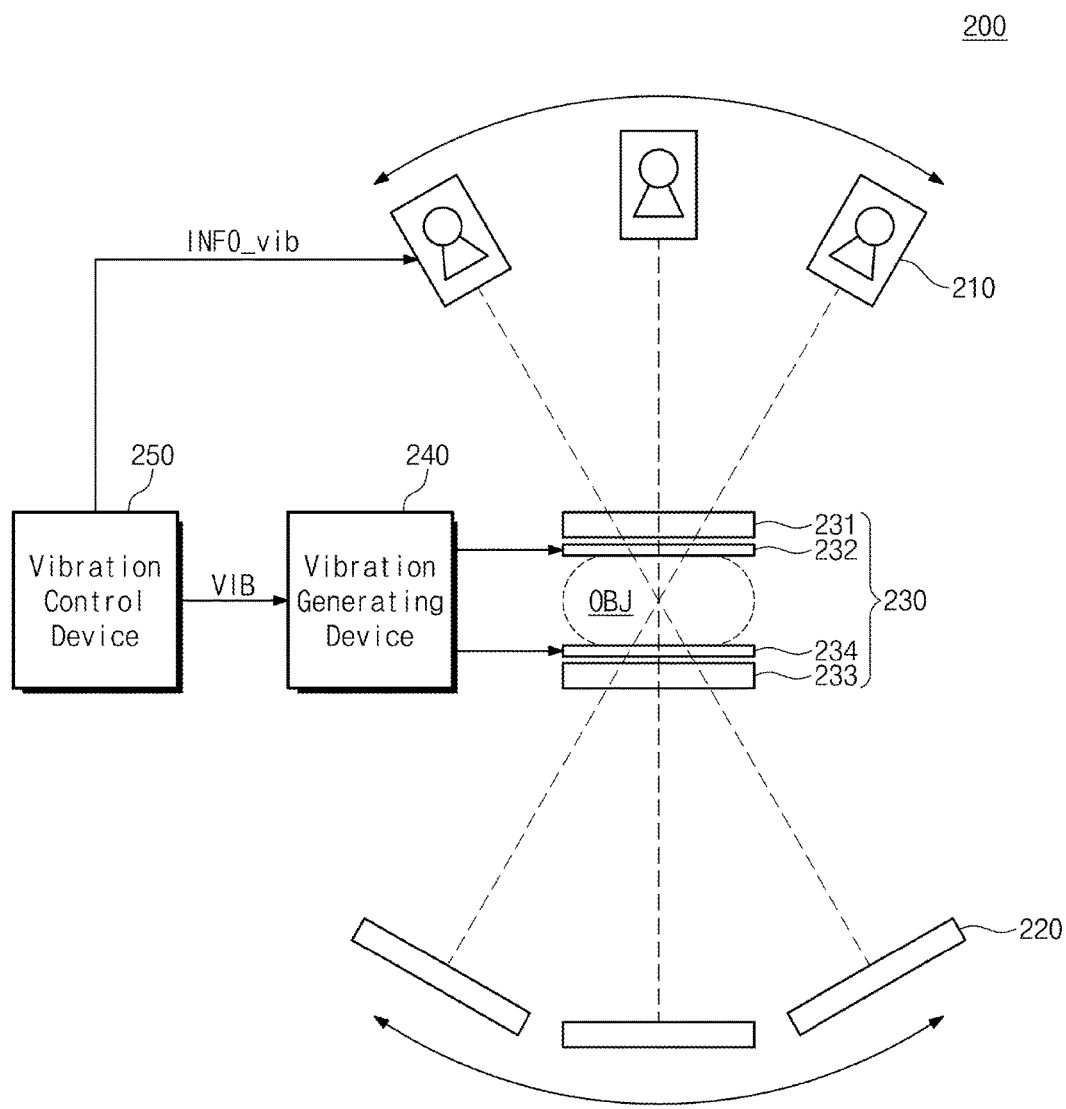
FIG. 4 is a view illustrating a digital breast tomosynthesis system according to another embodiment of the inventive concept.

FIG. 4 is a view illustrating a digital breast tomosynthesis system according to another embodiment of the inventive concept. Referring to FIG. 4, a digital breast tomosynthesis system 200 may include an X-ray generator 210, an X-ray detector 220, an object fixing unit 230, a vibration generating device 240, and a vibration control device 250. In the digital breast tomosynthesis system 200, the X-ray generator 210 and the X-ray detector 220 may be rotated around an object OBJ. Accordingly, the digital breast tomosynthesis system 200 may provide an ordinary DBT image and an elastic DBT image.

The X-ray generator 210 may irradiate the object OBJ by generating X-ray. For example, the X-ray generator 210 may include an X-ray tube. X-ray projected from the X-ray generator 210 may include photons having a plurality of energy levels.

X-ray may be projected from the X-ray generator 210 over a plurality of times for a specific time period. For example, X-ray may be projected from the X-ray generator 210 about 20 times to about 30 times for one second. X-ray may be projected from the X-ray generator 210 at regular intervals for a specific time period. Alternatively, X-ray may be projected from the X-ray generator 210 at intervals different from each other for a specific time period.

The X-ray generator 210 may receive vibration displacement information INFO_vib from the vibration control device 250. For example, the X-ray generator 210 may adjust the number and intervals of X-ray projection on the basis of the vibration displacement information INFO_vib. The X-ray may be projected from the X-ray generator 210 synchronously with the vibration of a first vibrating plate 232 and the second vibrating plate 234 on the basis of the vibration displacement information INFO_vib.

The object fixing unit 210 may be rotated around the object OBJ. For example, the X-ray generator 210 may irradiate the object OBJ at a first position. Also, the X-ray generator 210 may irradiate the object OBJ at a second position after being rotated around the object OBJ by a set angle. Also, the X-ray detector 220 may be rotated so as to be located at the reverse side to the X-ray generator 210 with respect to the object OBJ. For example, the X-ray detector 220 may be rotated by a set angle synchronously with the X-ray generator 210.

The X-ray detector 220 may detect an X-ray image passing through the object OBJ. For example, the X-ray detector 220 may detect photons projected from the X-ray generator 210 to thereby obtain an X-ray image passing through the object OBJ. The X-ray detector 220 may include an X-ray detecting element. As the X-ray detecting element, an element of an amorphous silicon (a-Si) type, a complementary metal oxide silicon (CMOS) type, an amorphous selenium (a-Se) type, or the like may be used. For elements of the amorphous silicon type and the CMOS type, a method of firstly converting X-ray into visible light by using a planar scintillator and then converting the visible light again into an electrical signal is used. On the contrary, for the amorphous selenium type, a method of directly converting X-ray into an electrical signal by using a photoelectric phenomenon is used. For example, the X-ray detector 220 has a plurality of detecting elements arrayed in a two-dimensional shape. The X-ray detector 220 may be located at the reverse side to the X-ray generator 210 with respect to the object OBJ.

The object fixing unit 230 may fix the object OBJ. Also, the object fixing unit 230 may compress the object OBJ. For example, the fixing part 230 may include a first fixing plate 231, a first vibrating plate 232, a second fixing plate 233, and a second vibrating plate 234. The first and second fixing plates 231 and 233 may be moved in the vertical direction. The object OBJ may be fixedly positioned or compressed through the movements of the first and second fixing plates 231 and 233. The first and second fixing plates 231 and 233 may be rotated around the object OBJ.

The first vibration plate 232 may be vertically moved in linkage with the first fixing plate 231. The second vibration plate 234 may be vertically moved in linkage with the second fixing plate 233. The object OBJ may be fixedly positioned or compressed between the first and second vibration plates 232 and 234. The first and second vibrating plates 232 and 234 may be vibrated according to the control of the vibration generating device 240.

The vibration generating device 240 may vibrate the first and second vibrating plates 232 and 234 in response to a vibration control signal VIB. For example, the vibration control signal VIB may be a voltage signal. The vibration generating device 240 may adjust the vibration frequencies of the first and second vibrating plates 232 and 234 according to the voltage level of the vibration control signal VIB.

The vibration control device 250 may control the overall operation of the vibration generating device 240. For example, the vibration control device 250 may generate the vibration control signal VIB according to a target frequency. The vibration control device 250 may store the value of the vibration control signal VIB corresponding to vibration frequencies in a look-up table form. Also, the vibration control device 250 may provide the X-ray generator 210 with the vibration displacement information INFO_vib. The vibration displacement information INFO_vib may include the vibration frequency information of the first and second vibrating plates 232 and 234.

The digital breast tomosynthesis system 200 according to an embodiment of the inventive concept may capture X-ray images from various measuring angles around the object OBJ. The digital breast tomosynthesis system 200 may provide an ordinary DBT images by reconstructing the images obtained from various measuring angels. Also, X-ray may be projected from the digital breast tomosynthesis system 200 synchronously with the vibration of the first and second vibrating plates 232 and 234 from various measuring angles. In the digital breast tomosynthesis system 200, a plurality of X-ray images synchronized with the vibration of the first and second vibrating plates 232 and 234 may be obtained from each of various measuring angles. Accordingly, in the digital breast tomosynthesis system 200, an elastic DBT image may be obtained by reconstructing the obtained X-ray images.

Figure 5:
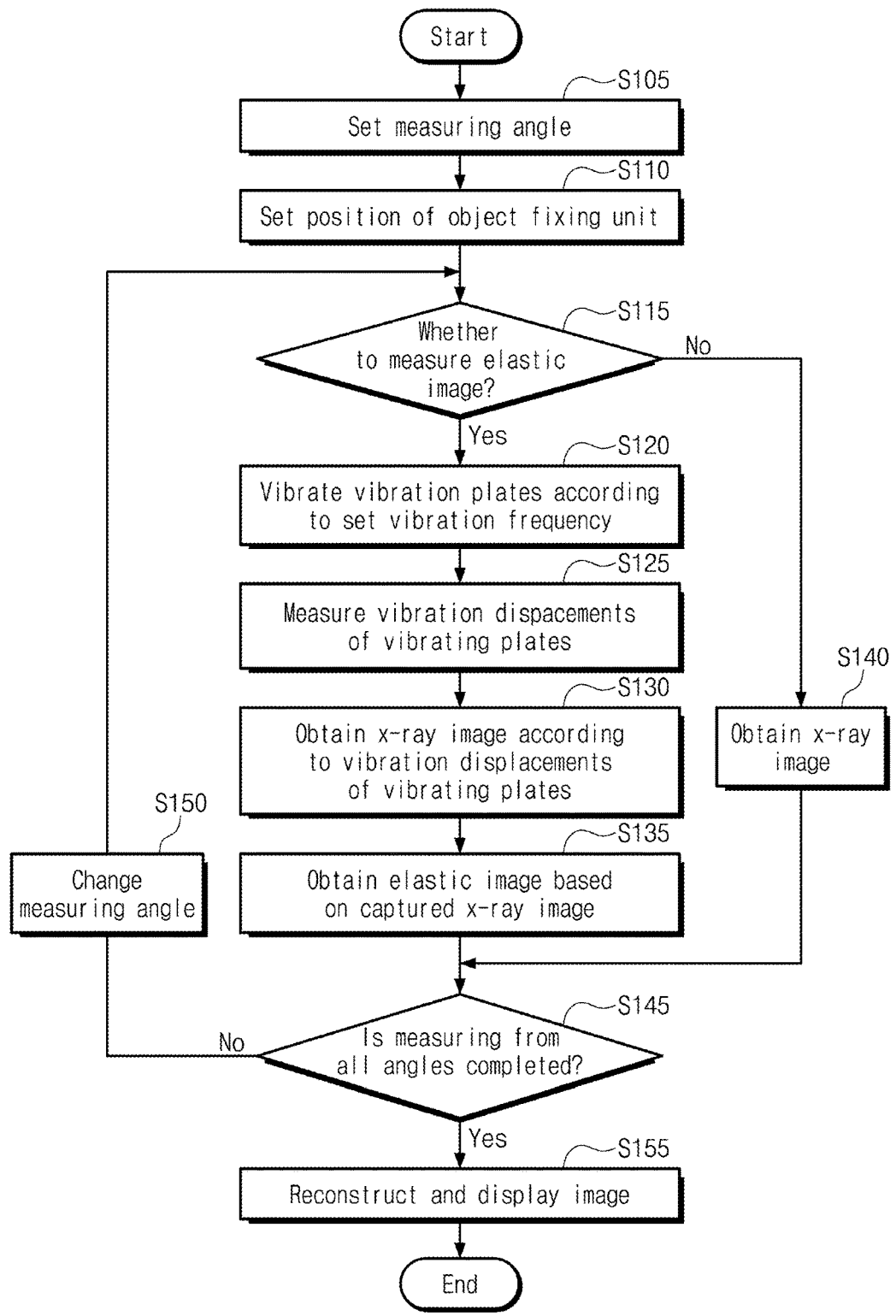
FIG. 5 is a flowchart illustrating a digital breast tomosynthesis method according to an embodiment of the present invention.

FIG. 5 is a flowchart illustrating a digital breast tomosynthesis method according to an embodiment of the present invention. Referring to FIGS. 4 and 5, a digital breast tomosynthesis system 200 may be operated in one of an ordinary DBT mode or an elastic DBT mode. The digital breast tomosynthesis system 200 may provide both an ordinary DBT image and an elastic DBT image through a series of sequence.

In step S105, the digital breast tomosynthesis system 200 may set measuring angles. For example, the digital breast tomosynthesis system 200 may position an X-ray generator 210 and an X-ray detector 220 according to the set measuring angles.

In step S110, the digital breast tomosynthesis system 200 may set a position of an object fixing unit 230. For example, the digital breast tomosynthesis system 200 may adjust first and second fixing plates 231 and 233 according to the set position. Here, first and second vibration plates 232 and 234 may be moved in linkage with the first and second fixing plates 231 and 233. An object OBJ may be fixes and compressed between the first and second vibrating plates 232 and 234.

In step S115, the digital breast tomosynthesis system 200 may determine whether an elastic image is measured. When the elastic image is measured, the process is moved to step S120. When an ordinary X-ray image is measured, the process is moved to step S140.

In step S120, the digital breast tomosynthesis system 200 starts operations for providing the elastic image. The digital breast tomosynthesis system 200 may vibrate the first and second vibrating plates 232 and 234 according to a set vibrating frequency. For example, a vibration control device 250 may generate a vibration control signal VIB to a vibration generating device 240. The vibration generating device 240 may vibrate the first and second vibrating plates 232 and 234 according to a set vibration frequency on the basis of the vibration control signal VIB. The first and second vibration plates 232 and 234 may vibrate while synchronized with each other.

In step S125, the digital breast tomosynthesis system 200 may measure the vibration displacement of the first and second vibrating plates 232 and 234. For example, the vibration control device 250 may provide the X-ray generator 210 with vibration displacement information INFO_vib. Alternatively, the digital breast tomosynthesis system 200 may measure the vibration displacement of the first and second vibration plates 232 and 234 using a separate displacement measuring device (see FIG. 7). The displacement measuring device may measure the vibration displacements of the first and second vibration plates 232 and 234 to generate vibration displacement information INFO_vib.

In step S130, the digital breast tomosynthesis system 200 may obtain an X-ray image according to the vibration displacements of the first and second vibrating plates 232 and 234. For example, the X-ray generator 210 may adjust the number and intervals of X-ray projection on the basis of the vibration displacement information INFO_vib. The X-ray detector 220 may obtain a plurality of X-ray images according to X-ray projected according to a set time interval.

In step S135, the digital breast tomosynthesis system 200 may obtain the elastic image on the basis of captured X-ray images. For example, the digital breast tomosynthesis system 200 may reconstruct the X-ray images. The digital breast tomosynthesis system 200 may derive a displacement image by calculating changes of the X-ray images according to a unit displacement. The digital breast tomosynthesis system 200 may reconstruct the elastic image using the derived displacement image.

In step S140, when determined not to measure the elastic image in step S115, the digital breast tomosynthesis system 200 may obtain an ordinary X-ray image.

In step S145, the digital breast tomosynthesis system 200 may determine whether X-ray image measurement corresponding to all predetermined angles is completed. When the X-ray image measurement corresponding to all predetermined angles is completed, the process is moved to step S155. When the X-ray image measurement corresponding to all predetermined angles is not completed, the process is moved to step S150.

In step S150, when the X-ray image measurement corresponding to all predetermined angles is not completed, the digital breast tomosynthesis system 200 may change the angle of the X-ray detector 220. Then, the digital breast tomosynthesis system 200 may repeat performing steps S115 to S140.

In step S155, when the X-ray image measurement corresponding to all predetermined angles is completed, the digital breast tomosynthesis system 200 may reconstruct and display the captured X-ray images or elastic images. For example, the digital breast tomosynthesis system 200 may provide an ordinary DBT images on the basis of X-ray images measured from various angels. Also, the digital breast tomosynthesis system 200 may obtain an elastic image on the basis of X-ray images measured by vibrating the object OBJ at each angle.

Also, the digital breast tomosynthesis system 200 may provide an elastic DBT image by integrating elastic images obtained from various angles. For example, the digital breast tomosynthesis system 200 may adjust the amount of generated vibration displacements of the first and second vibration plates 232 and 234 and the X-ray projection interval to obtain a plurality of elastic images. The digital breast tomosynthesis system 200 may obtain nth-degree displacement images of these elastic images using an nth difference formula. Also, the digital breast tomosynthesis system 200 may obtain an elastic DBT image using nth-degree displacement images.

That is, the digital breast tomosynthesis system 200 may provide both an ordinary DBT image and an elastic DBT image through a series of measuring sequence.

Figure 6:
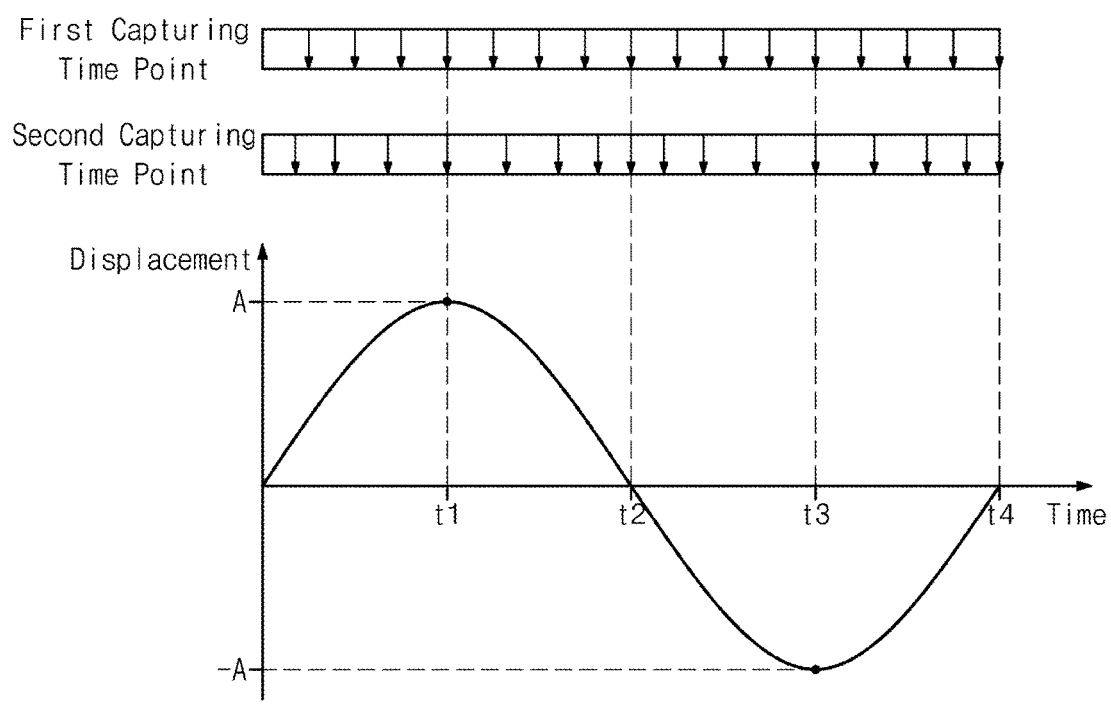
FIG. 6 is a view illustrating a method for obtaining an X-ray image according to a vibration displacement of a vibrating plate of FIG. 5.

FIG. 6 is a view illustrating a method for obtaining an X-ray image according to a vibration displacement of a vibrating plate of FIG. 5. Referring to FIGS. 4 to 6, the digital breast tomosynthesis system 200 may obtain an X-ray image according to a specific time interval while vibrating an object OBJ according to a set vibration frequency.

According to the set vibration frequency, the object OBJ may vibrate between maximum displacements A, and −A. For example, FIG. 6 is a graph illustrating a change in a vibration displacement of an object OBJ for one period. The object OBJ may respectively have maximum displacements A and −A at first and third time points t1 and t3.

Referring to a first capturing time, the digital breast tomosynthesis system 200 may project X-ray 16 times for one vibration period. Also, the digital breast tomosynthesis system 200 may project X-ray at regular time intervals.

Referring to a second capturing time, the digital breast tomosynthesis system 200 may project X-ray 16 times for one vibration period. Also, the digital breast tomosynthesis system 200 may project X-ray at time intervals different from each other. For example, before and after the first and third time points t1 and t3, changes in the vibration displacements are small. Before and after second and fourth time points t2 and t4 changes in the vibration displacements are large. Accordingly, the digital breast tomosynthesis system 200 may project X-ray at shorter intervals at the second and fourth time points t2 and t4 than those at the first and third time points t1 and t3.

The number of X-ray projections and the intervals between X-ray projections are all exemplary ones. Accordingly, the digital breast tomosynthesis system 200 may variously adjust the number of X-ray projections and the intervals between X-ray projections.

Figure 7:
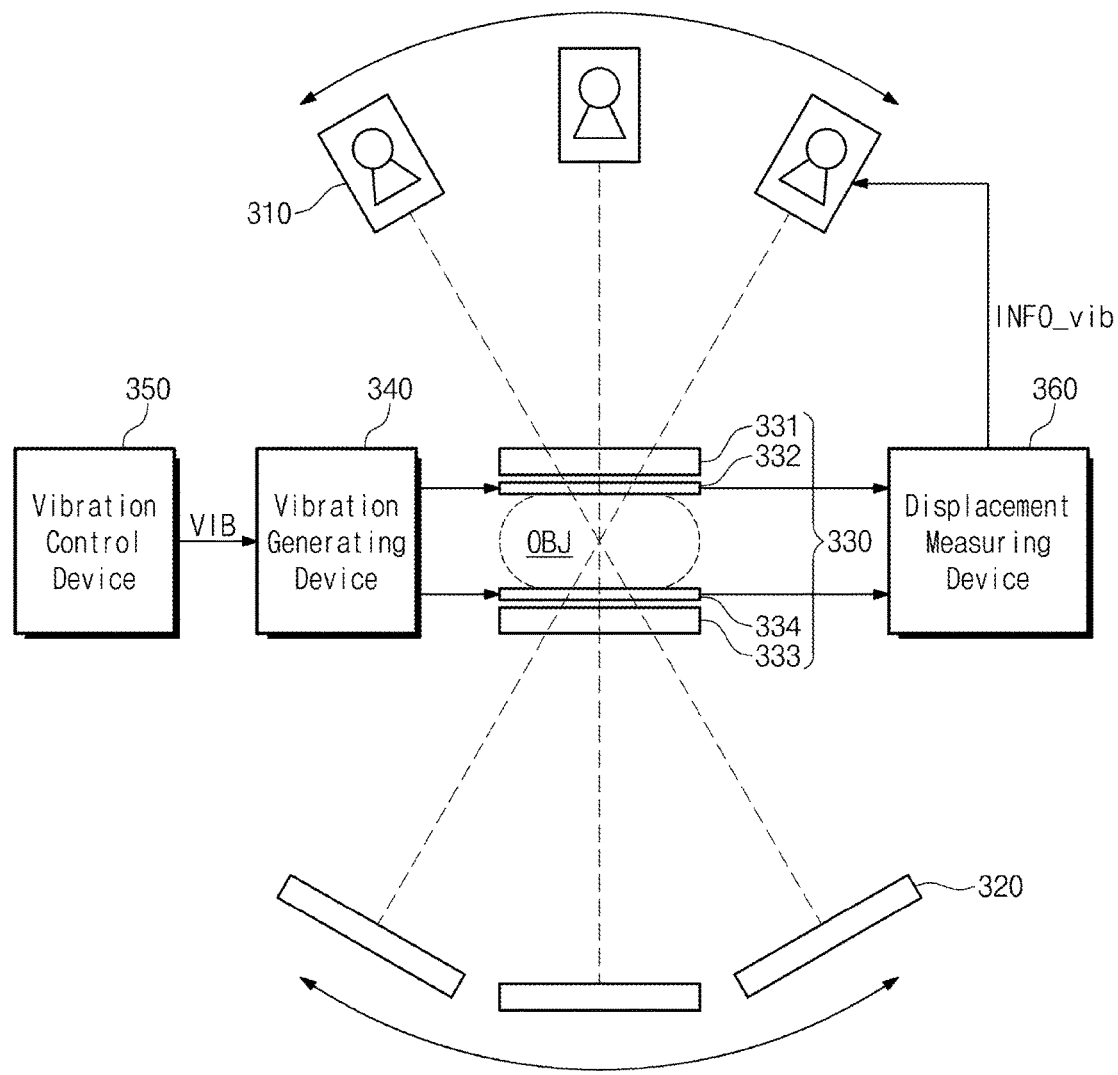
FIG. 7 is a view illustrating a digital breast tomosynthesis system according to another embodiment of the inventive concept.

FIG. 7 is a view illustrating a digital breast tomosynthesis system according to another embodiment of the inventive concept. Referring to FIG. 7, a digital breast tomosynthesis system 300 may include an X-ray generator 310, an X-ray detector 320, an object fixing unit 330, a vibration generating device 340, a vibration control device 350, and a displacement measuring device 360. In the digital breast tomosynthesis system 300, the X-ray generator 310 and the X-ray detector 320 may be rotated around an object OBJ. Accordingly, the digital breast tomosynthesis system 300 may provide an ordinary DBT image and an elastic DBT image. The digital breast tomosynthesis system 300 may measure vibration displacements of first and second vibrating plates 332 and 334. Accordingly, the digital breast tomosynthesis system 300 may project X-ray at more accurate time points for the elastic DBT image.

The X-ray generator 310 may irradiate the object OBJ by generating X-ray. For example, the X-ray generator 310 may include an X-ray tube. X-ray projected from the X-ray generator 310 may include photons having a plurality of energy levels.

X-ray may be projected from the X-ray generator 310 over a plurality of times for a specific time period. For example, X-ray may be projected from the X-ray generator 310 about 20 times to about 30 times for one second. The X-ray generator 310 may project X-ray at regular intervals for a specific time period. Alternatively, the X-ray generator 310 may project X-ray at intervals different from each other for a specific time period.

The X-ray generator 310 may receive vibration displacement information INFO_vib from the displacement measuring device 350. For example, the X-ray generator 310 may adjust a number and intervals of X-ray projection on the basis of the vibration displacement information INFO_vib. The X-ray generator 310 may project X-ray synchronously with the vibration of a first vibrating plate 332 and the second vibrating plate 334 on the basis of the vibration displacement information INFO_vib.

The X-ray generator 310 may be rotated around the object OBJ. For example, the X-ray generator 310 may irradiate the object OBJ with X-ray at a first position. Also, the X-ray generator 310 may irradiate the object OBJ at a second position after being rotated around the object OBJ by a set angle. Also, the X-ray detector 320 may be rotated so as to be located at the reverse side to the X-ray generator 310 with respect to the object OBJ. For example, the X-ray detector 320 may be rotated by a set angle synchronously with the X-ray generator 310.

The X-ray detector 320 may detect an X-ray image passing through the object OBJ. For example, the X-ray detector 320 may detect photons projected from the X-ray generator 310 to obtain an X-ray image passing through the object OBJ. The X-ray detector 320 may include an X-ray detecting element. As the X-ray detecting element, an element of an amorphous silicon (a-Si) type, a complementary metal oxide silicon (CMOS) type, an amorphous selenium (a-Se) type, or the like may be used. For elements of the amorphous silicon type and the CMOS type, a method of firstly converting X-ray into visible light by using a planar scintillator and then converting the visible light again into an electrical signal is used. On the contrary, for the amorphous selenium type, a method of directly converting X-ray into an electrical signal by using a photoelectric phenomenon is used. For example, the X-ray detector 320 has a plurality of detecting elements arrayed in a two-dimensional shape. The X-ray detector 320 may be located at the reverse side to the X-ray generator 310 with respect to the object OBJ.

The object fixing unit 330 may fix the object OBJ. Also, the object fixing unit 330 may compress the object OBJ. For example, the fixing part 330 may include a first fixing plate 331, a first vibrating plate 332, a second fixing plate 333, and a second vibrating plate 334. The first and second fixing plates 331 and 333 may be moved in the vertical direction. The object OBJ may be fixedly positioned or compressed through the movements of the first and second fixing plates 331 and 333. The first and second fixing plates 331 and 333 may be rotated around the object OBJ.

The first vibration plate 332 may be vertically moved in linkage with the first fixing plate 331. The second vibration plate 334 may be vertically moved in linkage with the second fixing plate 333. The object OBJ may be fixedly positioned or compressed between the first and second vibration plates 332 and 334. The first and second vibrating plates 332 and 334 may be vibrated according to the control of the vibration generating device 340.

The vibration generating device 340 may vibrate the first and second vibrating plates 332 and 234 in response to a vibration control signal VIB. For example, the vibration control signal VIB may be a voltage signal. The vibration generating device 340 may adjust the vibration frequencies of the first and second vibrating plates 332 and 334 according to the voltage level of the vibration control signal VIB.

The vibration control device 350 may control the overall operation of the vibration generating device 340. For example, the vibration control device 350 may generate the vibration control signal VIB according to a target frequency. The vibration control device 350 may store the value of the vibration control signal VIB corresponding to vibration frequencies in a look-up table form.

The displacement measuring device 360 may measure the vibration displacements of the first and second vibration plates 332 and 334. Also, displacement measuring device 360 may provide the X-ray generator 310 with the measured vibration displacement information INFO_vib. The X-ray generator 310 may project X-ray at a more accurate time point using the actually measured vibration displacement information INFO_vib.

The digital breast tomosynthesis system 300 according to an embodiment of the inventive concept may capture X-ray images from various measuring angles around the object OBJ. The digital breast tomosynthesis system 300 may provide an ordinary DBT images by reconstructing the images obtained from various measuring angels. Also, the digital breast tomosynthesis system 300 may project X-ray synchronously with the vibration of the first and second vibrating plates 332 and 334 from various measuring angles. In the digital breast tomosynthesis system 300, a plurality of X-ray images synchronized with the vibration of the first and second vibrating plates 332 and 334 may be obtained from each of various measuring angles. Accordingly, the digital breast tomosynthesis system 300 may provide an elastic DBT image by reconstructing the obtained X-ray images.

According to an embodiment of the inventive concept, there may be provided an assist device for elastography used for a digital breast tomosynthesis system. Also, an ordinary DBT image and an elastic image may be obtained by using a system and a method for digital breast tomosynthesis using the assist device for elastography.

Hitherto, the best mode was disclosed in the drawings and specification. While specific terms were used, they were not used to limit the meaning or the scope of the present invention described in Claims, but merely used to explain the present invention. Accordingly, a person having ordinary skill in the art will understand from the above that various modifications and other equivalent embodiments are also possible. Hence, the real protective scope of the present invention shall be determined by the technical scope of the accompanying Claims.

What is claimed is:

1. A digital breast tomosynthesis system comprising:
    an object fixing unit including first and second fixing plates, a first vibration plate moved in linkage with the first fixing plate and a second vibration plate moved in linkage with the second fixing plate, and configured to fix the object between the first and second vibration plates;

an X-ray generator configured to project X-ray toward the object;

an X-ray detector configured to detect the X-ray;

a vibration generating device configured to vibrate the first and second vibration plates at a set frequency; and a vibration control device configured to control the vibration generating device by generating a vibration signal corresponding to the set frequency, wherein the X-ray generator projects the X-ray at specific time intervals on the basis of the set frequency.

2. The digital breast tomosynthesis system of claim 1, wherein the vibration control device provides vibration displacement information about the first and second vibration plates to the X-ray generator to determine the specific time intervals.

3. The digital breast tomosynthesis system of claim 1, further comprising a displacement measuring device configured to generate the vibration displacement information for measuring displacements of the first and second vibration plates.

4. The digital breast tomosynthesis system of claim 3, wherein the X-ray generator determines the specific time intervals on the basis of the vibration displacement information received from the displacement measuring device.

5. The digital breast tomosynthesis system of claim 1, wherein the specific time intervals are set to equal intervals for one period of a vibration displacement of the object.

6. The digital breast tomosynthesis system of claim 1, wherein the specific time intervals comprises a plurality of time intervals changing according to a setting for one period of a vibration displacement of the object.

7. The digital breast tomosynthesis system of claim 6, wherein the greater a width of the vibration displacement of the object, the greater the time intervals of the specific time intervals.

8. The digital breast tomosynthesis system of claim 1, wherein
the X-ray detector is positioned on the reverse side of the X-ray generator with respect the object, and
the X-ray generator and the X-ray detector are rotated around the object according to a set angle.

9. The digital breast tomosynthesis system of claim 1, wherein the vibration generating device comprises:
a first fluid container positioned between the first fixing plate and the first vibration plate;
a second fluid container positioned between the second fixing plate and the second vibration plate; and
a fluid control device configured to adjusting a fluid pressure of a buffer fluid filled into the first and second containers,
wherein the fluid control device controls the fluid pressure of the buffer fluid such that the first and second vibration plates vibrate at the set frequency according to the vibration control signal.

10. The digital breast tomosynthesis system of claim 1, wherein the vibration generating device includes a vibrator for vibrating the first and second vibration plates at the set frequency according to the vibration control signal.

11. A vibration generation assist device used for a digital breast tomosynthesis system for capturing an X-ray image of an object, comprising:
an object fixing unit including first and second fixing plates, a first vibration plate moved in linkage with the first fixing plate and a second vibration plate moved in linkage with the second fixing plate, and configured to fix the object between the first and second vibration plates;
a first fluid container positioned between the first fixing plate and the first vibration plate;
a second fluid container positioned between the second fixing plate and the second vibration plate; and
a fluid control device configured to adjusting a fluid pressure of a buffer fluid filled into the first and second containers,
wherein the fluid control device controls the fluid pressure of the buffer fluid such that the first and second vibration plates vibrate at a set frequency according to the vibration control signal.

12. The vibration generation assist device of claim 11, wherein the first and second fluid containers are formed of a soft film and thereby have sizes varying with the fluid pressure of the buffer fluid corresponding to the set frequency.

13. The vibration generation assist device of claim 11, further comprising a vibration guide connected to the first and second vibrating plates to control the first and second plates so as to vibrate in a specific direction.

14. The vibration generation assist device of claim 11, wherein the first and second vibration plates vibrate synchronously with each other according to the set frequency.

15. A digital breast tomosynthesis method for a digital breast tomosynthesis system which comprises first and second fixing plates, a first vibration plate moved in linkage with the first fixing plate and a second vibration plate moved in linkage with the second fixing plate, and configured to fix an object between the first and second vibration plates, comprising:
setting positions of the first and second fixing plates and the first and second vibration plates;
setting a measuring angle for irradiating the object with X-ray;
determining whether to measure an elastic image;
vibrating the first and second vibration plates according to a set vibration frequency when the elastic image is measured;
measuring vibration displacements of the first and second vibration plates;
obtaining a plurality of X-ray images by irradiating the object with the X-ray according to the vibration displacements; and
generating the elastic image on the basis of the X-ray images.

16. The digital breast tomosynthesis method of claim 15, wherein in determining whether to measure the elastic image, when the elastic image is not measured, the object is irradiated with the X-ray without vibrating the first and second vibration plates.

17. The digital breast tomosynthesis method of claim 15, further comprising ensuring whether measuring is completed for all the set measuring angles, wherein when the measuring is not completed for all the set measuring angles, the measuring angle is changed, and the determining whether to measure the elastic image to the generating the elastic image are repeated.

18. The digital breast tomosynthesis method of claim 17, wherein when the measuring is completed for all the set measuring angles, an elastic digital breast tomosynthesis (DBT) image is generated on the basis of the plurality of X-ray images.

* * * * *